US012570656B2

(12) United States Patent
Williams

(10) Patent No.: US 12,570,656 B2
(45) Date of Patent: Mar. 10, 2026

(54) PURINE COMPOUNDS FOR TREATING DISORDERS

(71) Applicant: MARVEL BIOTECHNOLOGY, Calgary (CA)

(72) Inventor: Mark Williams, Calgary (CA)

(73) Assignee: MARVEL BIOTECHNOLOGY, Calgary (CA)

( * ) Notice: Subject to any disclaimer, the term of this patent is extended or adjusted under 35 U.S.C. 154(b) by 665 days.

(21) Appl. No.: 17/910,529

(22) PCT Filed: Mar. 9, 2021

(86) PCT No.: PCT/CA2021/050313
§ 371 (c)(1),
(2) Date: Sep. 9, 2022

(87) PCT Pub. No.: WO2021/179074
PCT Pub. Date: Sep. 16, 2021

(65) Prior Publication Data

US 2023/0151011 A1 May 18, 2023

Related U.S. Application Data

(60) Provisional application No. 62/987,533, filed on Mar. 10, 2020.

(51) Int. Cl.

| | |
|---|---|
| ***A61P 25/24*** | (2006.01) |
| ***A61P 25/16*** | (2006.01) |
| ***A61P 25/22*** | (2006.01) |
| ***C07D 473/06*** | (2006.01) |
| ***C07D 473/22*** | (2006.01) |

(52) U.S. Cl.
CPC ............ *C07D 473/22* (2013.01); *A61P 25/16* (2018.01); *A61P 25/22* (2018.01); *A61P 25/24* (2018.01); *C07D 473/06* (2013.01)

(58) Field of Classification Search
CPC ............................ C07D 473/22; C07D 473/06
See application file for complete search history.

(56) References Cited

U.S. PATENT DOCUMENTS

| | | | | |
|---|---|---|---|---|
| 5,484,920 | A | 1/1996 | Suzuki | |
| 5,543,415 | A | 8/1996 | Suzuki | |
| 5,587,378 | A | 12/1996 | Suzuki | |
| 7,727,993 | B2 * | 6/2010 | Kase .................... | A61K 31/522 514/263.34 |
| 2005/0176739 | A1 | 8/2005 | Hara | |

FOREIGN PATENT DOCUMENTS

| | | | |
|---|---|---|---|
| CA | 2112031 | A1 | 6/1994 |
| JP | H06211856 | A | 8/1994 |
| WO | 9401114 | A1 | 1/1994 |
| WO | 2001032182 | A1 | 5/2001 |
| WO | 2003063876 | A2 | 8/2003 |
| WO | 2013058681 | A2 | 4/2013 |

OTHER PUBLICATIONS

Silverman (The Organic Chemistry of Drug Design and Drug Action, Academic Press. Inc., 19-23). (Year: 1992).*
Patani et al. (Chem. Rev., pp. 3147-3176). (Year: 1996).*
Shah et al. (Journal of Enzyme Inhibition and Medicinal Chemistry, 22(5), 527-540). (Year: 2007).*
Cronstein B. "Adenosine receptors and fibrosis: a translational view", F1000 Biol Rep. 2011; 3: 21.
Domenici MR et al. "Adenosine A2A receptor as potential therapeutic target in neuropsychiatric disorders", Pharmacol Res 2019; 147: 104338.
Pasquini, S. et al., Adenosine Receptors in Neuropsychiatric Disorders: Fine Regulators of Neurotransmission and Potential Therapeutic Targets., Int. J. Mol. Sci. 2022, 23, 1219. https://dol.org/10.3390/ijms23031219.
Robert D. Leone, Ying-Chun Lo, and Jonathan D. Powell, "A2aR antagonists: Next generation checkpoint blockade for cancer immunotherapy", Comput Struct Biotechnol J. 2015; 13: 265-272.
Extended European Search Report issued for corresponding application No. EP 21768628.6, mailed Jun. 4, 2024.
Office Action issued by the China National Intellectual Property Administration for corresponding application No. CN 202180020893.4, mailed Mar. 8, 2024.
Office Action issued by the Japan Patent Office for corresponding application No. JP 2022-55485, mailed Mar. 4, 2025.
Supplemental Partial European Search Report issued for corresponding application No. EP 21768628.6, mailed Mar. 12, 2024.

* cited by examiner

*Primary Examiner* — Susanna Moore
(74) *Attorney, Agent, or Firm* — Renner, Otto, Boisselle & Sklar, LLP.

(57) ABSTRACT

Novel and known substituted purine compounds and salts thereof act as adenosine A2a receptor (A2aR) antagonists for cancer immunotherapy, depression, anxiety, multiple sclerosis, NASH, scleroderma, ADHD, Alzheimer's and Parkinsons. Pharmaceutical compositions comprising such compounds, and methods of their use in treating depression are also taught.

11 Claims, 12 Drawing Sheets

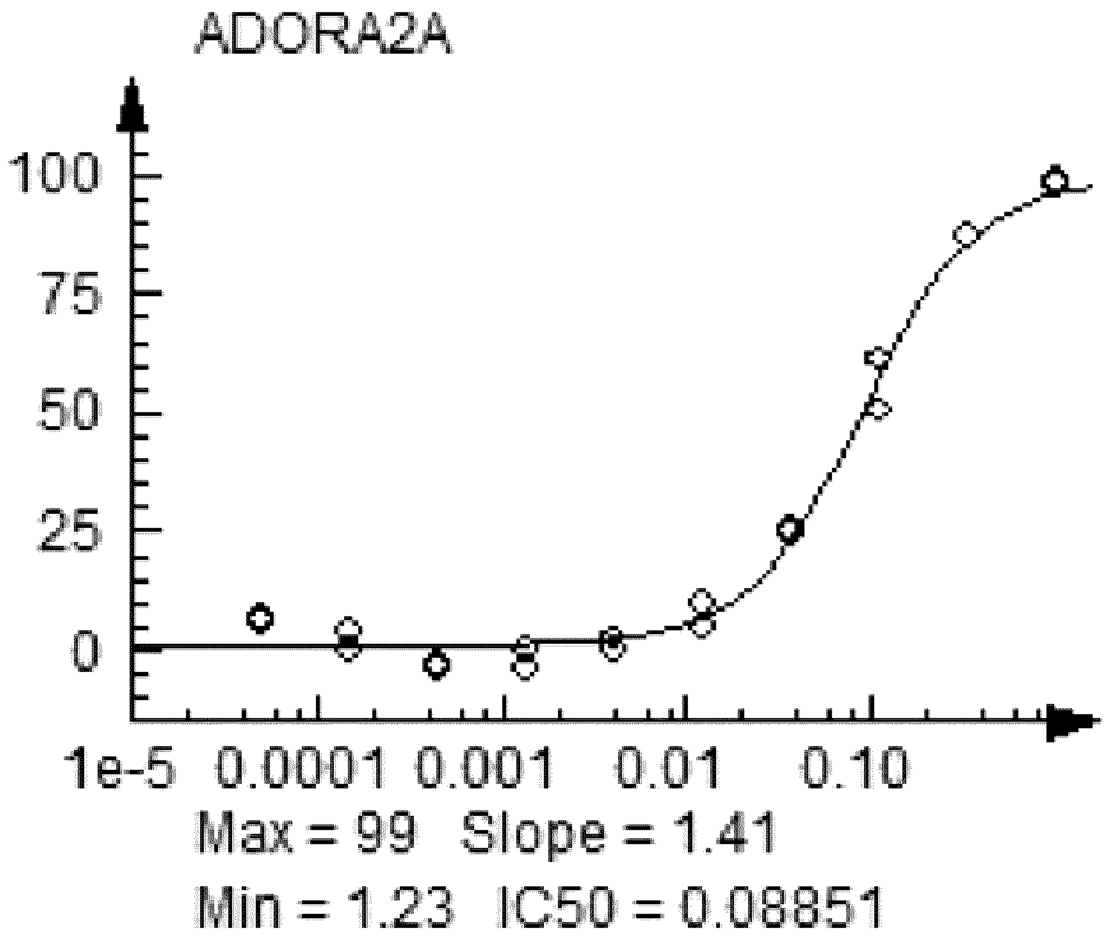
FIG. 1 – (I)

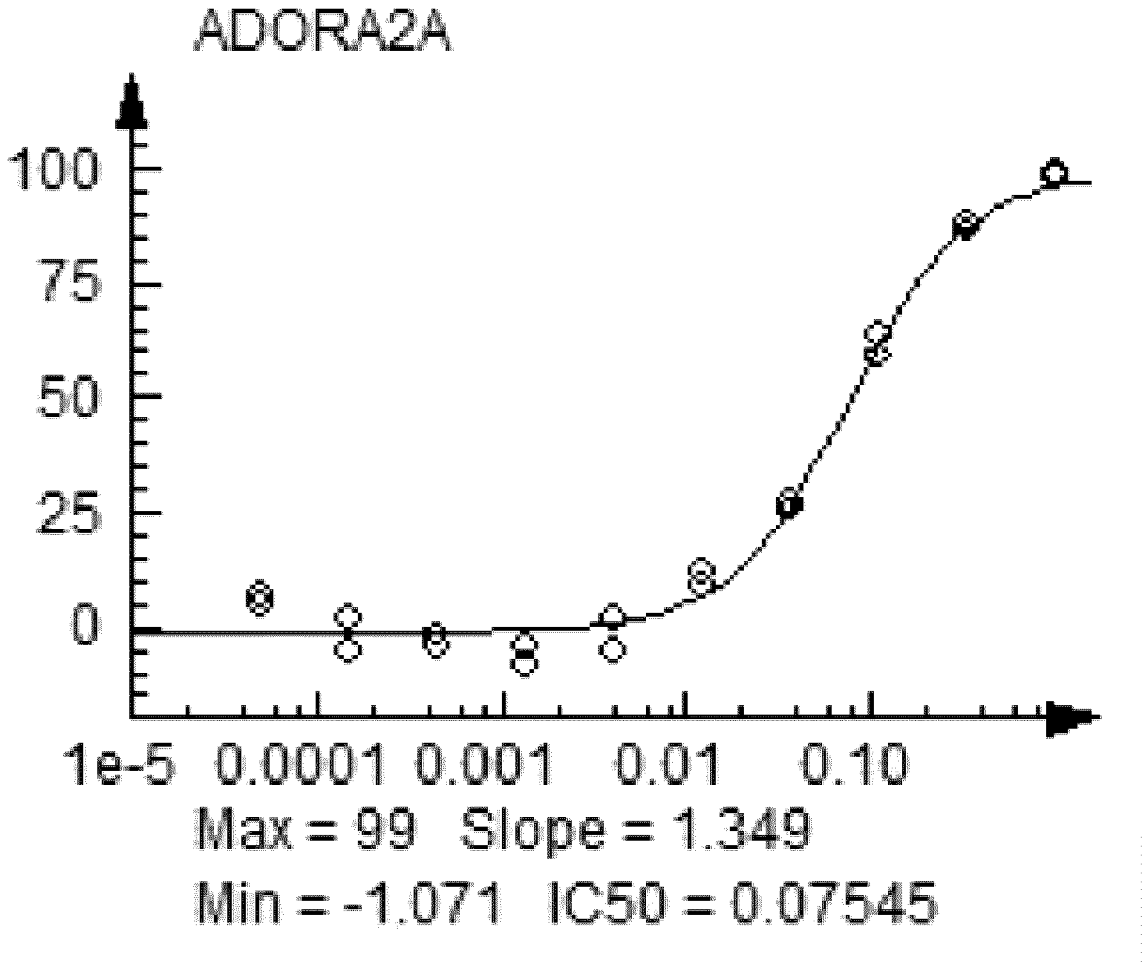
FIG. 2 – (II)

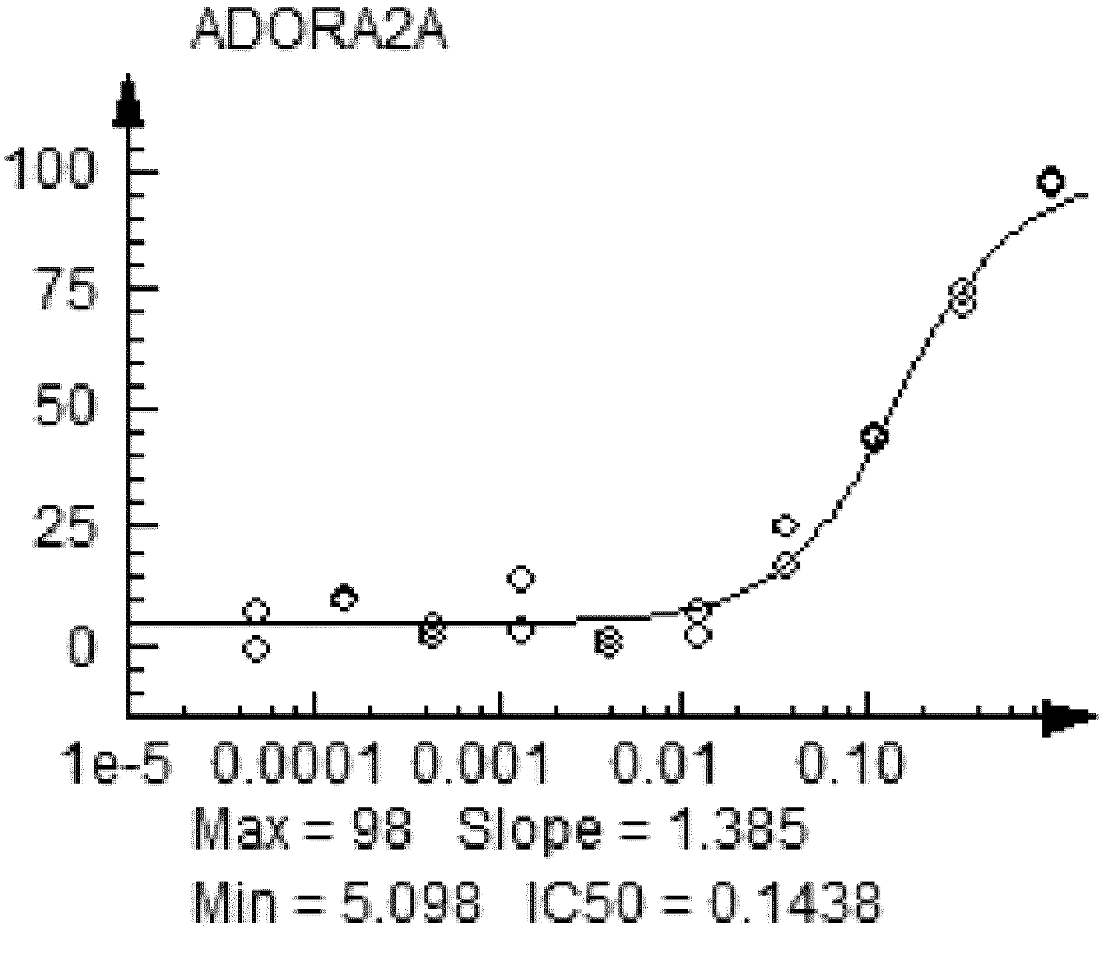
FIG. 3 – (III) SD-007

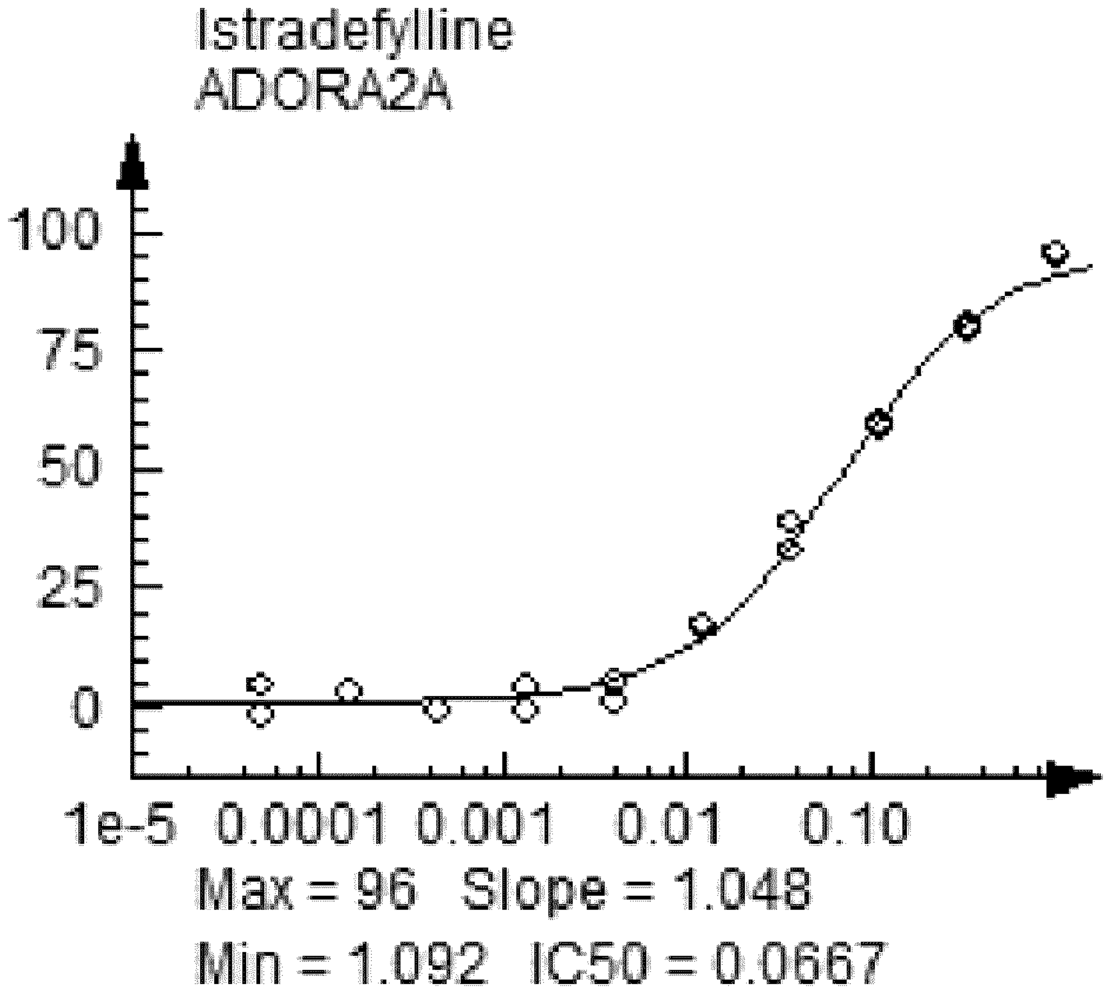
FIG. 4 – (IV) istradefyline

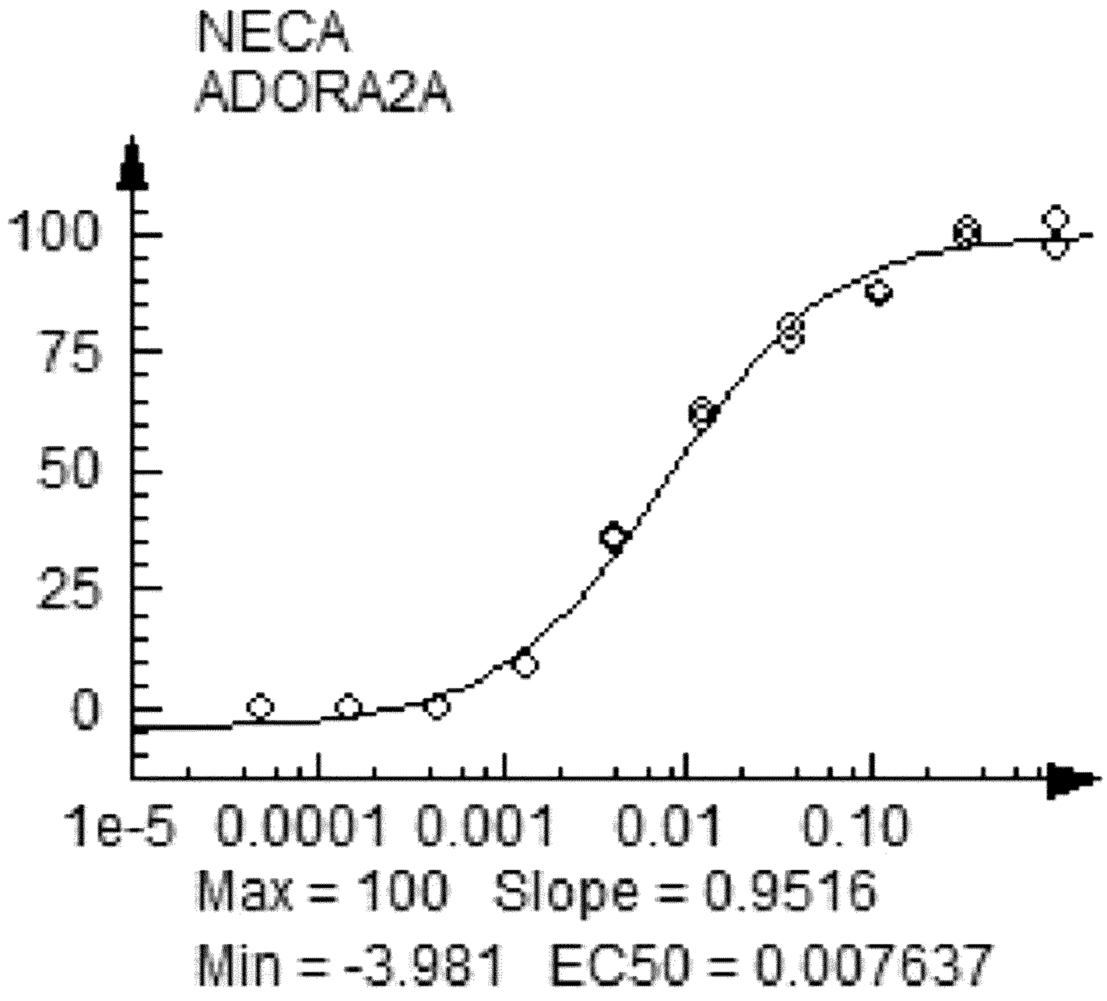
FIG. 5 - NECA

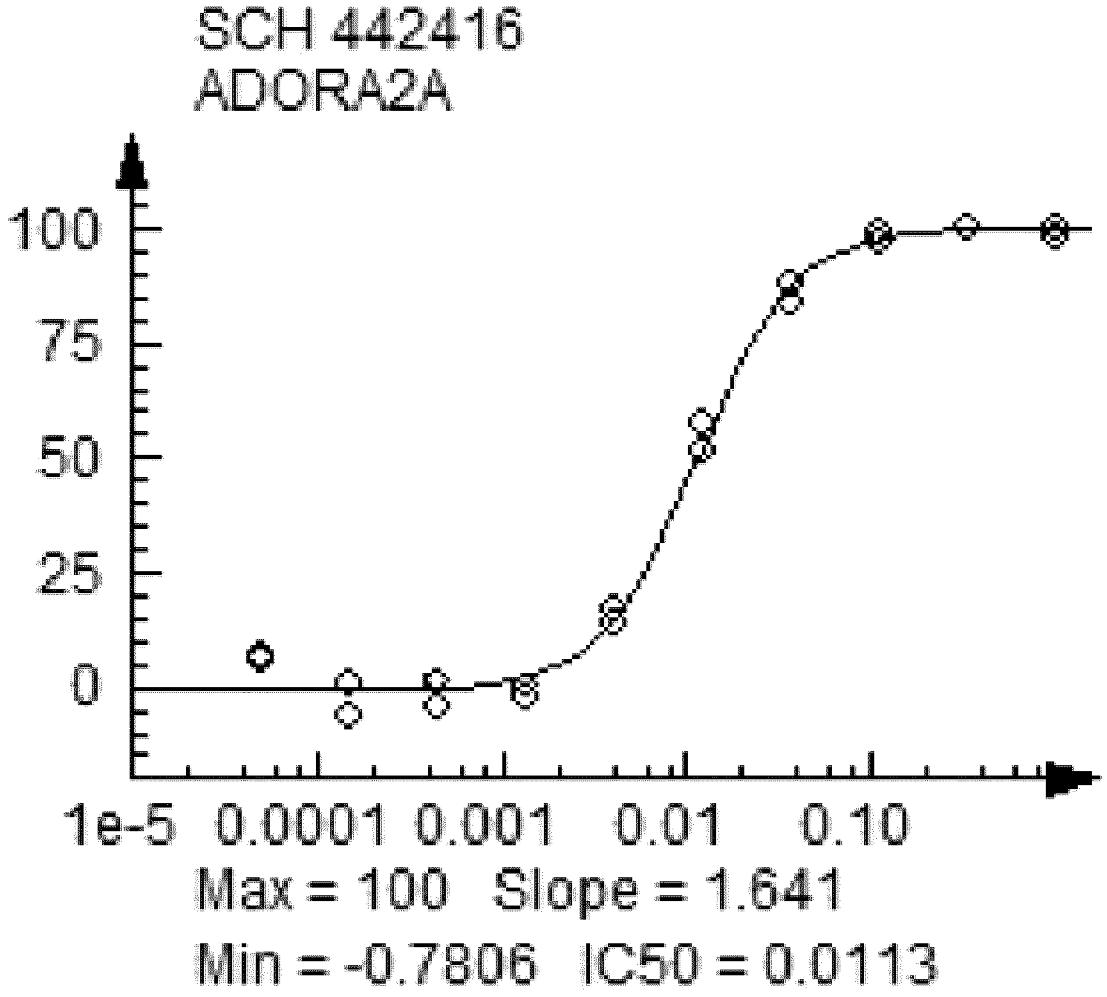
FIG. 6 – SCH 442416

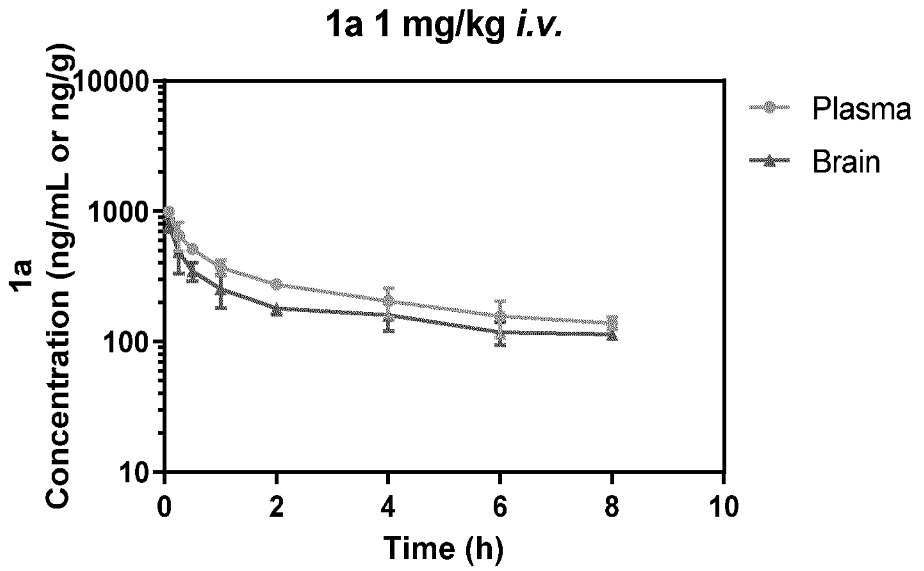
FIG. 7 - (I)
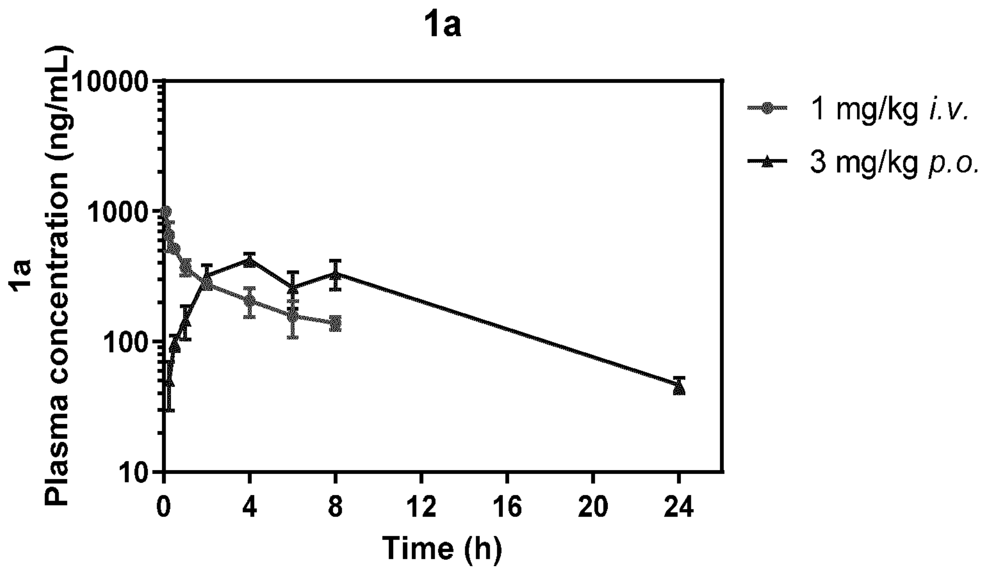
FIG. 8 – (I)

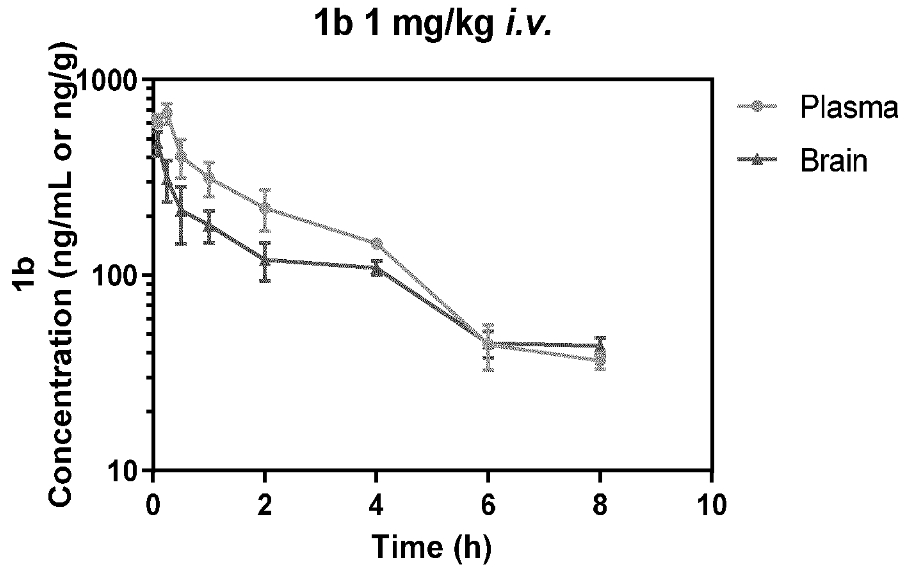
FIG. 9 – (II)
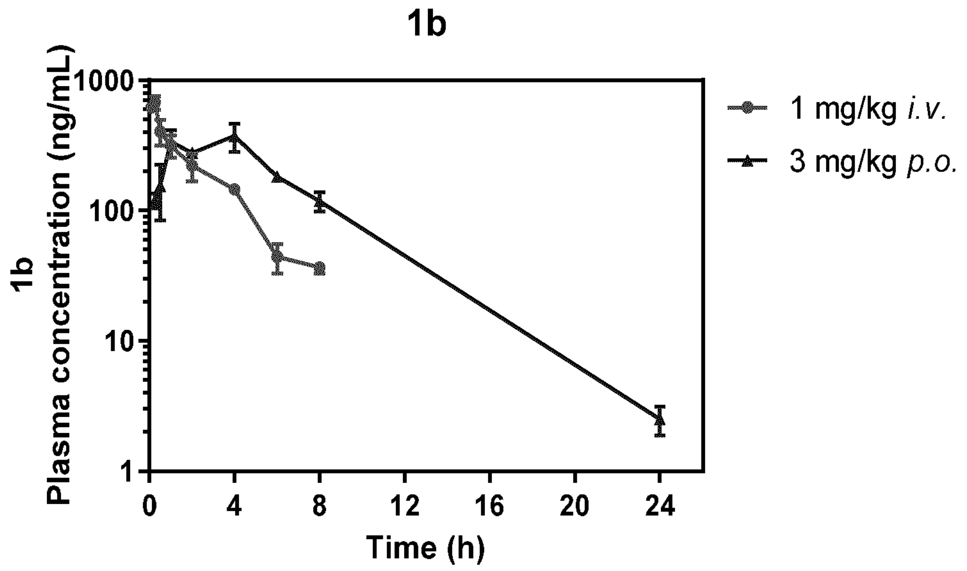
FIG. 10 – (II)

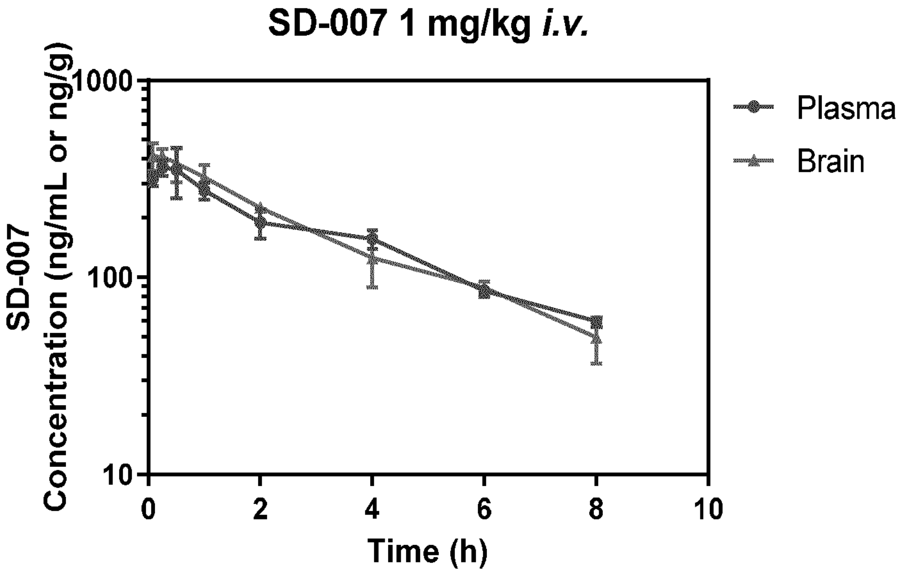
FIG. 11 – (III) SD-007
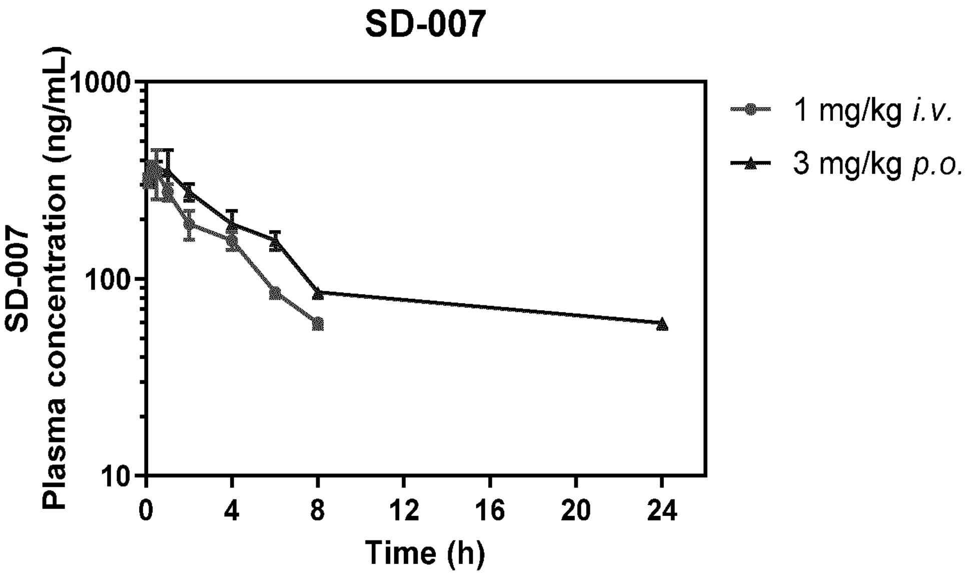
FIG. 12 (III), SD-007

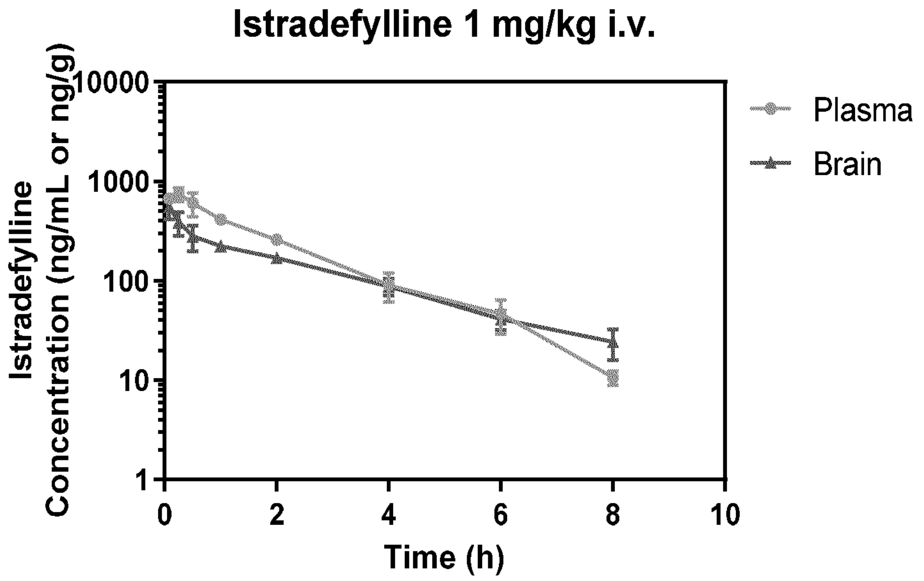
FIG. 13 – (IV) istradefyline
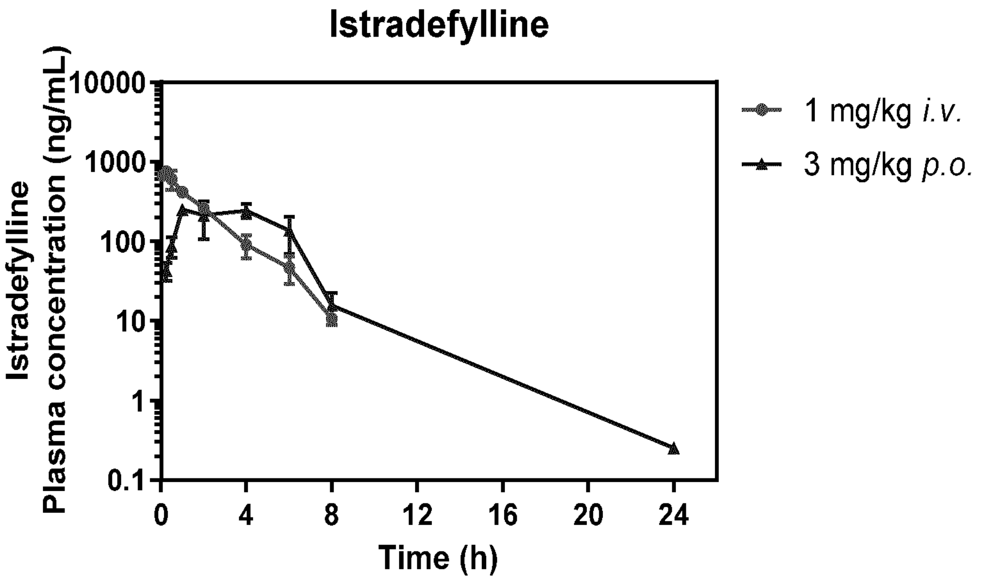
FIG. 14– (IV) istradefyline

PURINE COMPOUNDS FOR TREATING DISORDERS

This application is a national phase of International Application No. PCT/CA2021/050313 filed Mar. 9, 2021, which claims priority to U.S. Provisional Application No. 62/987,533, filed Mar. 10, 2020, each of which is hereby incorporated by reference in its entirety.

FIELD OF THE INVENTION

This invention relates generally to substituted purine compounds and salts thereof acting as adenosine A2a receptor (A2aR) antagonists for cancer, depression, anxiety, multiple sclerosis, NASH, sclerodermascleroderma, ADHD, Alzheimer's and Parkinsons, pharmaceutical compositions comprising such compounds, and methods of their use in treating cancer, depression, anxiety, multiple sclerosis, NASH, scleroderma, ADHD, Alzheimer's and Parkinsons.

BACKGROUND OF THE INVENTION

Adenosine realizes its biological actions through a class of membrane specific receptors that belong to the super family of receptors coupled with G proteins. At least four subtypes of adenosine receptors have been identified: A1, A2a, A1b, and A3.

A2aR has been shown to provide a regulatory role in the immune system. One A2aR antagonist, istradefylline, has been shown to reduce motor impairment and in turn improve function in neurodegenerative diseases such as Parkinson's disease and related movement disorders (e.g. Huntington's Disease).

WO2013058681A2 discloses using A2aR antagonists for treating diseases of the central nervous system, oncological diseases and viral and bacterial diseases.

There is a need for A2aR antagonists that are suitable for treating neurological diseases, fibrosis related diseases (NASH and scleroderma) and cancer.

SUMMARY OF THE INVENTION

The inventors have found that certain purine compounds useful as A2aR antagonists for treating diseases such as depression.

In one aspect, a compound of Formula (I) or a pharmaceutically acceptable salt thereof is provided:

(I)

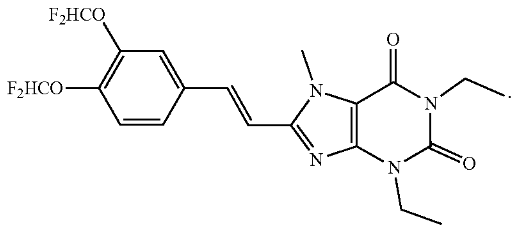

8-[(E)-2-[3,4-bis(difluoromethoxy)phenyl]vinyl]-1,3-diethyl-7-methyl-purine-2,6-dione;hydrofluoride In one aspect, a compound of Formula (II) or a pharmaceutically acceptable salt thereof is provided:

(II)

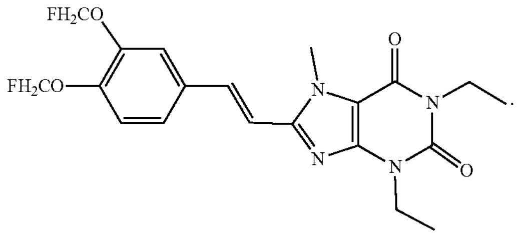

8-[(E)-2-[3,4-bis(difluoromethoxy)phenyl]vinyl]-1,3-diethyl-7-methyl-purine-2,6-dione In one aspect, a compound of Formula (III) or a pharmaceutically acceptable salt thereof is provided:

(III)

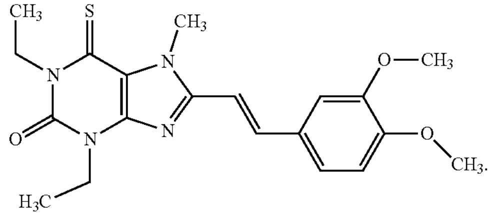

8-[(E)-2-(3,4-dimethoxyphenyl)vinyl]-1,3-diethyl-7-methyl-6-thioxo-purin-2-one

In one aspect, it is found that Istradefylline, E)-8-(3,4-Dimethoxystyryl)-1,3-diethyl-7-methylxanthine, of Formula (IV), or a pharmaceutically acceptable salt thereof, is an A2aR antagonist that may be useful for treating cancer, depression, anxiety, multiple sclerosis, NASH, scleroderma, ADHD, Alzheimer's and Parkinsons:

(IV)

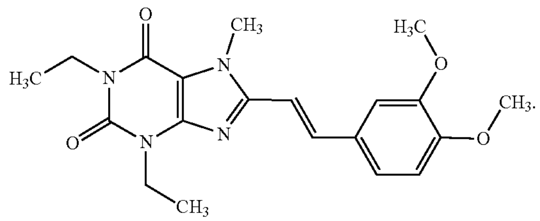

In one aspect, it is found that SCH 442416, 2-(2-Furanyl)-7-[3-(4-methoxyphenyl)propyl]-7H-pyrazolo [4,3-e][1,2,4]triazolo[1,5-c]pyrimidin-5-amine, of Formula (V), or a pharmaceutically acceptable salt thereof, is an A2aR antagonist that may be useful for treating cancer, depression, anxiety, multiple sclerosis, NASH, scleroderma, ADHD, Alzheimer's and Parkinsons:

(V)

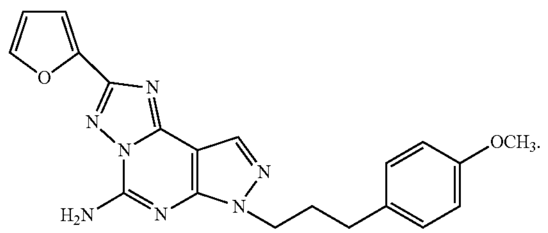

The disclosure also includes a pharmaceutical composition comprising a therapeutically effective amount of one or more of the compounds of formulae I, II, and III, and pharmaceutically acceptable salts thereof, and a pharmaceutically acceptable excipient.

This disclosure further includes a method for treating depression using one or more of the compounds of formulae I, II, and III and pharmaceutically acceptable salts thereof are provided. The method comprises administering the one or more compound to a subject in need of such treatment, thereby treating depression.

This disclosure further includes a method for treating cancer, anxiety, multiple sclerosis, NASH, scleroderma, ADHD, Alzheimer's or Parkinsons using one or more of the compounds of formulae I, II, and III, and pharmaceutically acceptable salts thereof are provided. The method comprises administering the one or more compound to a subject in need of such treatment, thereby treating depression, anxiety, multiple sclerosis, NASH, scleroderma, ADHD, Alzheimer's and Parkinsons.

In some embodiments, the compound are administered by intravenous injection, by injection into tissue, intraperitoneally, orally, or nasally. In some embodiments, the composition have a form of a solution, dispersion, suspension, powder, capsule, tablet, pill, time release capsule, time release tablet, or time release pill.

Method for synthesizing the compounds for formulae I, II and III are provided.

The disclosure encompasses a method comprising providing at least one such compound, measuring inhibition of A2aR activity for the compound and determining if the inhibition is above the expected level.

BRIEF DESCRIPTION OF THE DRAWINGS

FIG. 1 is a graph showing the GPCR screening result of the compound of formula I;

FIG. 2 is a graph showing the GPCR screening result of the compound of formula II;

FIG. 3 is a graph showing the GPCR screening result of the compound of formula III, SD-007;

FIG. 4 is a graph showing the GPCR screening result of the compound of formula IV, istradefyline;

FIG. 5 is a graph showing the GPCR screening result of 5'-N-Ethylcarboxamidoadenosine (NECA);

FIG. 6 is a graph showing the GPCR screening result of SCH 442416;

FIG. 7 is a graph showing plasma and brain concentrations of the compound of Formula I over time;

FIG. 8 is a graph showing the plasma concentrations over time after administration of 1 mg/kg i.v. or 3 mg/kg p.o of the compound of Formula I.

FIG. 9 is a graph showing plasma and brain concentrations of the compound of Formula II over time;

FIG. 10 is a graph showing the plasma concentrations over time after administration of 1 mg/kg i.v. or 3 mg/kg p.o of the compound of Formula II;

FIG. 11 is a graph showing plasma and brain concentrations of the compound of Formula III, SD-007 over time;

FIG. 12 is a graph showing the plasma concentrations over time after administration of 1 mg/kg i.v. or 3 mg/kg p.o of the compound of Formula III, SD-007;

FIG. 13 is a graph showing plasma and brain concentrations of the compound of Istradefiline (Formula IV) over time;

FIG. 14 is a graph showing the plasma concentrations over time after administration of 1 mg/kg i.v. or 3 mg/kg p.o of the compound of Formula IV;

DETAILED DESCRIPTION

Figure 15:
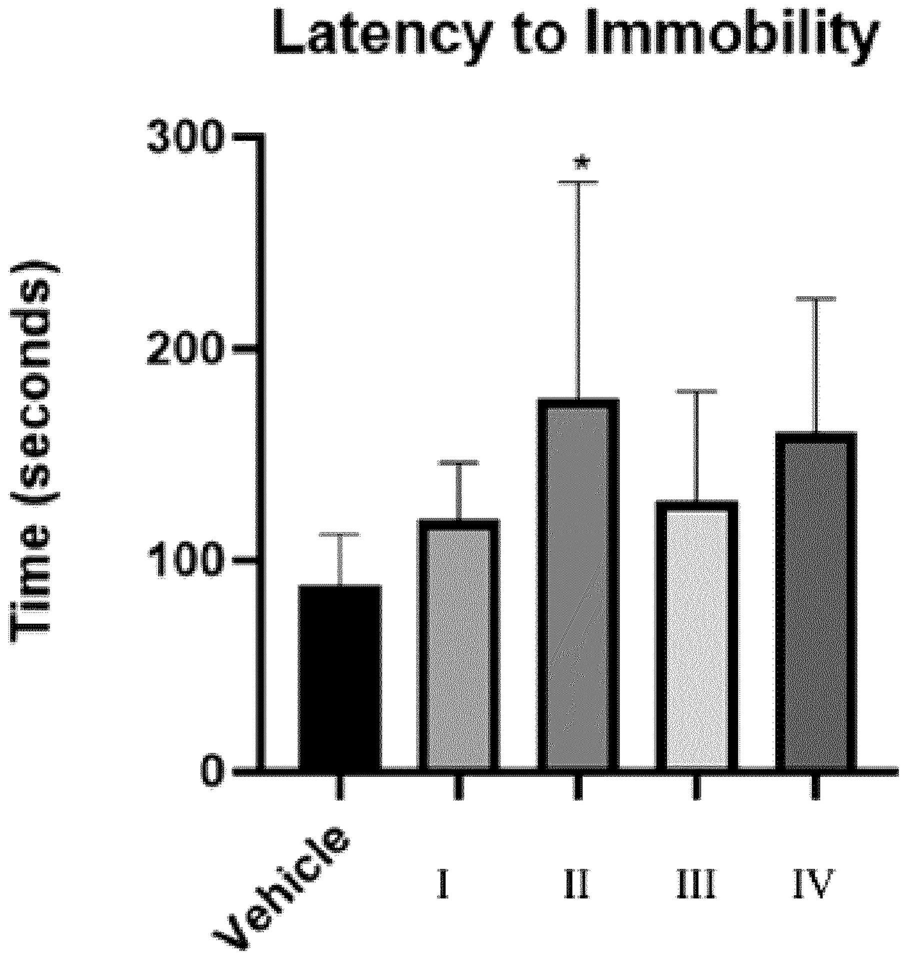
FIG. 15 is a graph comparing the time from latency to immobility for various compounds.

Embodiments of the disclosure are discussed in detail below. In describing embodiments, specific terminology is employed for the sake of clarity. However, the disclosure is not intended to be limited to the specific terminology so selected. A person skilled in the relevant art will recognize that other equivalent parts can be employed and other methods developed without parting from the spirit and scope of the disclosure. All references cited herein are incorporated by reference as if each had been individually incorporated.

Unless defined otherwise, all technical and scientific terms used herein have the same meaning as commonly understood by one of ordinary skill in the art to which this disclosure belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The terms "pharmaceutically effective amount", "therapeutically effective amount" or "therapeutically effective dose," "effective amount" refer to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The term "pharmaceutically acceptable salts" in this disclosure includes salts of the compounds of this disclosure that are prepared with relatively nontoxic acids or bases, depending on the particular substituents found on the compounds described herein. When compounds of the present disclosure contain relatively acidic functionalities, base addition salts may be obtained by contacting the neutral form of such compounds with a sufficient amount of the desired base, either neat or in a suitable inert solvent. For example, salts may be derived from pharmaceutically acceptable inorganic bases that include aluminum, ammonium, calcium, copper, ferric, ferrous, lithium, magnesium, manganic, manganous, potassium, sodium, zinc and the like. For example, salts may be derived from pharmaceutically acceptable organic bases that include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts may be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," Journal of Pharmaceutical Science, 66:1-19, 1977). Certain specific compounds of the present disclosure contain both basic and acidic functionalities that allow the compounds to be converted into either base or acid addition salts.

In some embodiments, the neutral forms of the compounds is regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The "subject" is defined herein to include animals such as mammals, including, but not limited to, primates (e.g., humans), cows, sheep, goats, horses, dogs, cats, rabbits, rats, mice and the like. In some embodiments, the subject is a human.

The terms "treat", "treating", "treatment" and grammatical variations thereof as used in this disclosure, include partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the disclosure may be applied preventively, prophylactically, pallatively or remedially.

The compounds of the present disclosure may also contain unnatural proportions of atomic isotopes at one or more of the atoms that constitute such compounds. For example, the compounds may be radiolabeled with isotopes, such as for example deuterium ($^2H$), tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure.

The inventors developed the compounds of formulae I and II, and developed efficient methods for preparing the compounds for formulae I and II:

Scheme 1

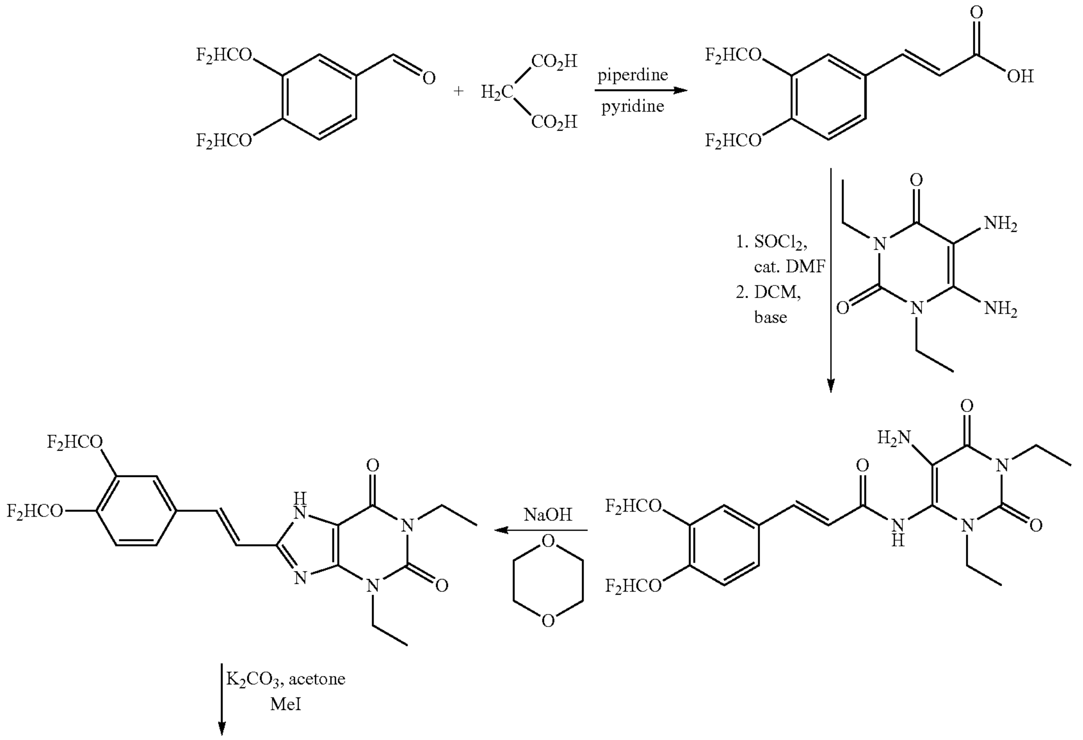

-continued
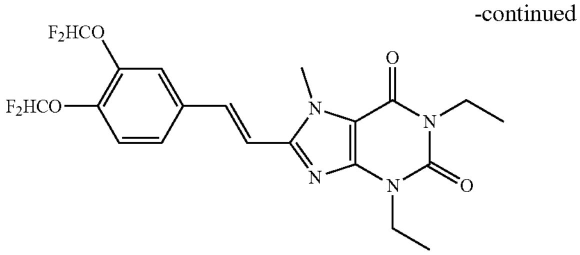
I
Scheme 2
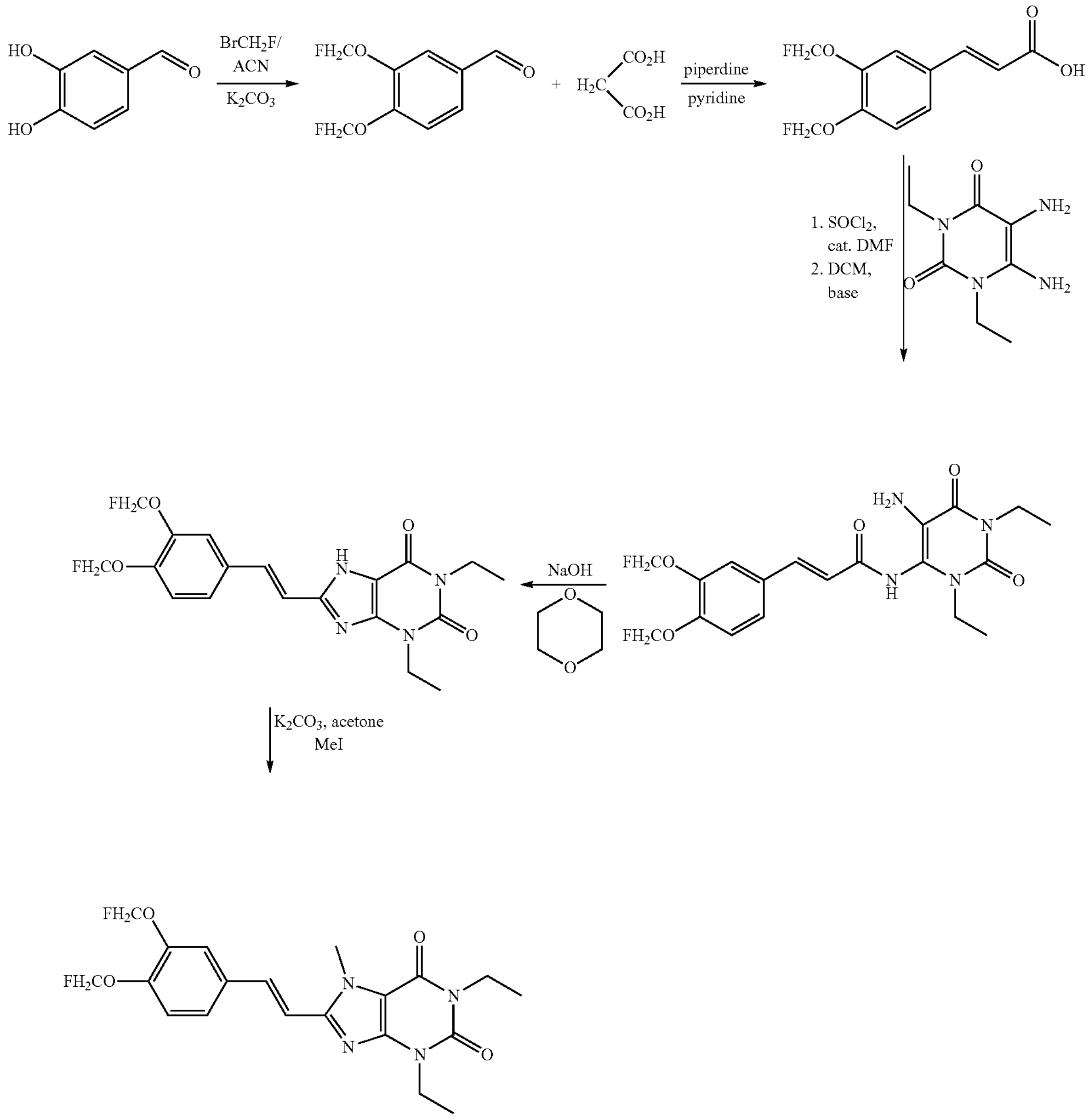
II

Scheme 3

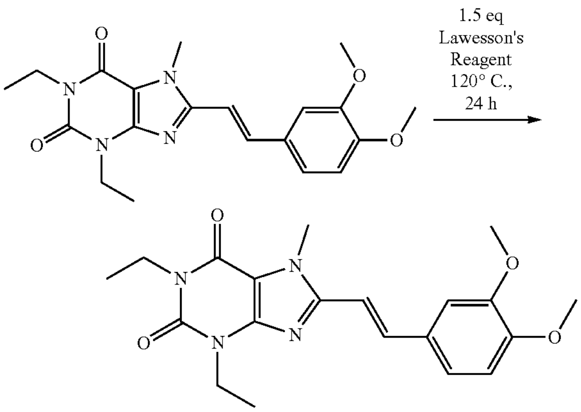

III

To ascertain whether the compounds are suitable A2aR antagonists, the compounds of formulae I, II, III, and IV were subjected to GPCR screening using A2aR as the target. The screening was done using the GPCR Screening and Profiling Services by Eurofins DiscoverX Corporation. For comparison, NECA and SCH 442416 were also screened. The results are shown in FIGS. 1-6 and the Experiments.

The screening results showed these compounds to have substantial A2aR antagonist properties.

Robert D. Leone, Ying-Chun Lo, and Jonathan D. Powell, "A2aR antagonists: Next generation checkpoint blockade for cancer immunotherapy", *Comput Struct Biotechnol J.* 2015; 13: 265-272, which is incorporated herein by reference in its entirety, discloses certain A2aR antagonists that can be useful for cancer immunotherapy. Thus, the compounds described herein are useful for treating cancer. Domenici M R et al. "Adenosine A2A receptor as potential therapeutic target in neuropsychiatric disorders", *Pharmacol Res* 2019; 147: 104338, which is incorporated herein by reference in its entirety, discloses certain A2aR antagonists can be useful for treating Alzheimer's disease, Parkinson's disease, attention-deficit hyperactivity disorder, fragile X syndrome, depression, anxiety. Thus the compounds herein are useful for treating neurological diseases. Cronstein B. "Adenosine receptors and fibrosis: a translational view", F1000 Biol Rep. 2011; 3: 21, which is incorporated herein by reference in its entirety, discloses certain A2aR antagonists could be useful in treating fibrosis, in particular hepatic fibrosis (e.g. NASH) and dermal fibrosis (e.g. scleroderma).

One or more of the compounds described herein is useful for treating cancer, depression, anxiety, multiple sclerosis, NASH, scleroderma, ADHD, Alzheimer's or Parkinsons.

In some embodiments, the compounds of the disclosure are useful in their pure forms. In some embodiments, the compounds of this disclosure are useful as pharmaceutical compositions prepared with a therapeutically effective amount of the compounds, as defined herein, and a pharmaceutically acceptable excipient, for example a carrier, or a diluent.

In some embodiments, the compounds are systemically administered, e.g., orally, in combination with a pharmaceutically acceptable vehicle such as an inert diluent or an assimilable edible carrier; or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with a fine inert powdered carrier and inhaled by the subject or insufflated. The percentage of the compositions and preparations may, of course, be varied and may be a suitable percentage of the weight of a given unit dosage form. The amount of compounds in such therapeutically useful compositions is such that an effective dosage level may be obtained.

In some embodiments, the tablets, troches, pills, capsules, or the like also contains the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. It is appreciated that a capsule may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. It is understood that any material used in preparing any unit dosage form should be pharmaceutically acceptable and substantially non-toxic in the amounts employed. In some embodiments, the compounds are incorporated into sustained-release preparations and devices. For example, the compounds may be incorporated into time release capsules, time release tablets, and time release pills.

In some embodiments, the compounds are administered intravenously or intraperitoneally by infusion or injection. Solutions of the compounds may be prepared in water, optionally mixed with a nontoxic surfactant. In some embodiments, dispersions are prepared in glycerol, liquid polyethylene glycols, triacetin, or mixtures thereof or in oils. In some embodiments, these preparations contain a preservative to prevent the growth of microorganisms under ordinary conditions of storage and use.

In some embodiments, the pharmaceutical dosage forms for injection or infusion is sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. In some embodiments, the liquid carrier or vehicle is a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. In some embodiments, the proper fluidity is maintained by the formation of liposomes, by the maintenance of the required particle size in the case of dispersions or by the use of surfactants. In some embodiments, various antibacterial and antifungal agents, for example, parabens, chlorobutanol, phenol, sorbic acid, thimerosal, and the like is used to prevent of the action of microorganisms. In some embodiments, isotonic agents, for example, sugars, buffers or sodium chloride is included. In some embodiments, agents delaying absorption, for example, aluminum monostearate or gelatin is used to prolong absorption of the injectable compositions.

In some embodiments, sterile injectable solutions is prepared by incorporating the compounds in the required amount in the appropriate solvent, and optionally with some of the other ingredients enumerated above, as may be required, followed by filter sterilization. In the case of sterile powders for the preparation of sterile injectable solutions, the composition may be vacuum dried and/or freeze dried, which yield a powder of the active ingredient plus any additional desired ingredient present in the previously sterile-filtered solutions.

In some embodiments, for topical administration, the compounds are applied in pure form. In some embodiments, the compounds are administered to the skin as compositions or formulations, in combination with a dermatologically acceptable carrier, which may be a solid or a liquid.

In some embodiments, the solid carriers include finely divided solids such as talc, clay, microcrystalline cellulose, silica, alumina and the like. In some embodiments, the solid carriers include nontoxic polymeric nanoparticles or microparticles. In some embodiments, the liquid carriers include water, alcohols or glycols or water/alcohol/glycol blends, in which the compounds can be dissolved or dispersed at effective levels, optionally with the aid of nontoxic surfactants. In some embodiments, adjuvants such as fragrances and additional antimicrobial agents are added to optimize the properties for a given use. The resultant liquid compositions may be applied from absorbent pads, used to impregnate bandages and other dressings, or sprayed onto the affected area using pump-type or aerosol sprayers.

In some embodiments, thickeners such as synthetic polymers, fatty acids, fatty acid salts and esters, fatty alcohols, modified celluloses or modified mineral materials are employed with liquid carriers to form spreadable pastes, gels, ointments, soaps, and the like, for application directly to the skin of the user.

In some embodiments, the compounds are formulated in lyophilized form for parenteral administration. In some embodiments, Lyophilized formulations is reconstituted by addition of water or other aqueous medium and then further diluted with a suitable diluent prior to use. In some embodiments, the liquid formulation is a buffered, isotonic, aqueous solution. In some embodiments, the diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

In some embodiments, the pharmaceutical composition may additionally contain one or more other pharmacologically active agents in addition to a compound described herein.

In some embodiments, useful dosages of the compounds may be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

It is appreciated that the amount of the compounds required for use in treatment will vary not only with the particular salt selected but also with the route of administration, the nature of the condition being treated and the age and condition of the patient and will be ultimately at the discretion of the attendant physician or clinician.

In some embodiments, effective dosages and routes of administration of agents of the disclosure are conventional. The exact amount (effective dose) of the compounds may vary from subject to subject, depending on, for example, the species, age, weight and general or clinical condition of the subject, the severity or mechanism of any disorder being treated, the particular compound or vehicle used, the method and scheduling of administration, and the like. In some embodiments, the therapeutically effective dose is determined empirically, by conventional procedures known to those of skill in the art. For example, persons skilled in the art may refer to The Pharmacological Basis of Therapeutics, Goodman and Gilman, eds., Macmillan Publishing Co., New York. In some embodiments, an effective dose is estimated initially either in cell culture assays or in suitable animal models. In some embodiments, the animal model is used to determine the appropriate concentration ranges and routes of administration. In some embodiments, such information is then used to determine useful doses and routes for administration in humans. In some embodiments, a therapeutic dose is selected by analogy to dosages for comparable therapeutic agents.

For example, the dosage may be in the range from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 0.3 mg/kg, 0.7 mg/kg, 1 mg/kg, 10 mg/kg, or 50 mg/kg of body weight per day.

In some embodiments, the compounds are administered in unit dosage form; for example, containing 0.05 to 10000 mg, 0.5 to 10000 mg, 5 to 1000 mg, or about 100 mg of active ingredient per unit dosage form.

In some embodiments, the compounds are administered to achieve peak plasma concentrations of, for example, from about 0.5 to about 75 μM, about 1 to 50 μM, about 2 to about 30 μM, or about 5 to about 25 μM. Exemplary desirable plasma concentrations include at least or no more than 0.25, 0.5, 1, 5, 10, 25, 50, 75, 100 or 200 μM. For example, plasma levels may be from about 1 to 100 micromolar or from about 10 to about 25 micromolar. In some embodiments, this is achieved by the intravenous injection of a 0.05 to 5% solution of the compounds, optionally in saline, or orally administered as a bolus containing about 1-100 mg of the compounds. In some embodiments, desirable blood levels is maintained by continuous infusion to provide about 0.00005-5 mg per kg body weight per hour, for example at least or no more than 0.00005, 0.0005, 0.005, 0.05, 0.5, or 5 mg/kg/hr. In some embodiments, such levels are obtained by intermittent infusions containing about 0.0002-20 mg per kg body weight, for example, at least or no more than 0.0002, 0.002, 0.02, 0.2, 2, 20, or 50 mg of the compounds per kg of body weight.

In an embodiment, the amount of purine compound used is between 0.1 to 5 mg per kg of the subject per day. In a preferred embodiment, the amount of purine compound used is between 0.2 to 1.3 mg per kg of the subject per day. In a further preferred embodiment, the amount of purine compound used is about 0.3 mg to 0.7 per kg of the subject per day.

In some embodiments, the compounds are presented in a single dose or as divided doses administered at appropriate intervals, for example, as two, three, four or more sub-doses per day. In some embodiments, the sub-dose itself is further divided, e.g., into a number of discrete loosely spaced administrations; such as multiple inhalations from an insufflator.

In some embodiments, a pharmaceutical composition of the present disclosure is packaged in a container with a label, or instructions, or both, indicating use of the pharmaceutical composition in the treatment of the indicated disease.

It is understood that one or more compounds of this disclosure may be used independently or in any combination thereof.

Example 1

The compounds of formulae I, II, III, and IV were screened for GPCR activity using A2aR as the target. For comparison, NECA and SCH 442416 were also screened. NECA is an A2aR agonist. SCH 442416 is an A2aR antagonists.

Assay Design: Calcium Mobilization

Cell Handling

Cell lines were expanded from freezer stocks according to standard procedures. Cells were seeded in a total volume of 20 μL into black-walled, clear-bottom, Poly-D-lysine coated 384-well microplates and incubated at 37° C. for the appropriate time prior to testing.

Dye Loading

Assays were performed in 1× Dye Loading Buffer consisting of 1× Dye, 1× Additive A and 2.5 mM Probenecid in HBSS/20 mM Hepes. Probenicid was prepared fresh. Cells were loaded with dye prior to testing. Media was aspirated from cells and replaced with 20 μL Dye Loading Buffer. Cells were incubated for 30-60 minutes at 37° C.

Agonist Format

For agonist determination, cells were incubated with sample to induce response. After dye loading, cells were removed from the incubator and 10 μL HBSS/20 mM Hepes was added. 3× vehicle was included in the buffer when performing agonist dose curves to define the EC80 for subsequent antagonist assays. Cells were incubated for 30 minutes at room temperature in the dark to equilibrate plate temperature. Intermediate dilution of sample stocks was performed to generate 4× sample in assay buffer. Compound agonist activity was measured on a FLIPR Tetra (MDS). Calcium mobilization was monitored for 2 minutes and 10 μL 4× sample in HBSS/20 mM Hepes was added to the cells 5 seconds into the assay.

Allosteric Modulation Format

For allosteric determination, cells were pre-incubated with sample followed by agonist induction at the EC20 concentration. Intermediate dilution of sample stocks was performed to generate 3× sample in assay buffer. After dye loading, cells were removed from the incubator and 10 μL 3× sample was added. Cells were incubated for 30 minutes at room temperature in the dark to equilibrate plate temperature. Vehicle concentration was 1%. Compound allosteric activity was measured on a FLIPR Tetra (MDS). Calcium mobilization was monitored for 2 minutes and 10 μL of 4×EC20 agonist in HBSS/20 mM Hepes was added to the cells 5 seconds into the assay.

Antagonist Format

For antagonist determination, cells were pre-incubated with sample followed by agonist challenge at the EC80 concentration. Intermediate dilution of sample stocks was performed to generate 3× sample in assay buffer. After dye loading, cells were removed from the incubator and 10 μL 3× sample was added. Cells were incubated for 30 minutes at room temperature in the dark to equilibrate plate temperature. Vehicle concentration was 1%. Compound antagonist activity was measured on a FLIPR Tetra (MDS). Calcium mobilization was monitored for 2 minutes and 10 μL EC80 agonist in HBSS/20 mM Hepes was added to the cells 5 seconds into the assay.

Data Analysis

Compound activity was analyzed using CBIS data analysis suite (ChemInnovation, CA). For agonist mode assays, percentage activity is calculated using the following formula:

% Activity=100%×(mean RFU of test sample−mean RFU of vehicle control)/(mean MAX RFU control ligand −mean RFU of vehicle control).

For positive allosteric mode assays, percentage modulation was calculated using the following formula:

% Modulation=100%×((mean RFU of test sample−mean RFU of EC20 control)/(mean RFU of MAX control ligand −mean RFU of EC20 control)).

For antagonist and negative allosteric modulation mode assays, percentage inhibition is calculated using the following formula:

% Inhibition=100%×(1−(mean RFU of test sample−mean RFU of vehicle control)/(mean RFU of EC80 control−mean RFU of vehicle control)).

FIGS. 1 to 6 present the results of G-protein-coupled receptors (GPCR) screening using A2aR as the target by the GPCR Screening and Profiling Services of Eurofins DiscoverX Corporation.

In the screening, the activation of the A2aR resulted in calcium mobilization, which was monitored using a calcium-sensitive dye. When the calcium was released, the fluorescence of the dye was increased and the increase was measured in real-time.

FIGS. 1 to 6 show percent reacted (Y) versus concentration in μM (X). Compounds were tested in antagonist mode with the requested GPCR Biosensor Assay. For the antagonist assay, data was normalized to the maximal and minimal response observed in the presence of EC80 ligand and vehicle. The following EC80 concentrations were used: ADORA2A Calcium Flux: 0.021 μM NECA.

FIG. 1 shows the result for the compound of formula I. The half maximal inhibitory concentration ($IC_{50}$) was 0.08851 μM.

FIG. 2 shows the result for the compound of formula I. The $IC_{50}$ was 0.07545 μM.

FIG. 3 shows the result for the compound of formula III. The $IC_{50}$ was 0.1438 μM.

FIG. 4 shows the result for the compound of formula IV, istradefyline. The $IC_{50}$ was 0.0667 μM.

FIG. 5 shows the result for NECA. The half maximal effective concentration ($EC_{50}$) was 0.007637 μM.

FIG. 6 shows the result for SCH 442416. The $IC_{50}$ was 0.0113 μM.

Summary of Results

| Compound Name | Assay Name | Assay Format | Assay Target | Result Type | RC50 | Unit | Hill | Curve Bottom | Curve Top | Max Response |
|---|---|---|---|---|---|---|---|---|---|---|
| NECA | Calcium Flux | Agonist | ADORA2A | EC50 | 0.00763748 | uM | 0.95163 | −3.9807 | 100 | 100.03 |
| SCH 442416 | Calcium Flux | Antagonist | ADORA2A | IC50 | 0.01130316 | uM | 1.6409 | −0.78065 | 100 | 99.962 |
| Istradefylline | Calcium Flux | Antagonist | ADORA2A | IC50 | 0.06669603 | uM | 1.0483 | 1.0923 | 96 | 95.231 |
| (III) | Calcium Flux | Antagonist | ADORA2A | IC50 | 0.1437812 | uM | 1.3853 | 5.0984 | 98 | 97.097 |
| (I) | Calcium Flux | Antagonist | ADORA2A | IC50 | 0.08851156 | uM | 1.4103 | 1.23 | 99 | 98.133 |
| (II) | Calcium Flux | Antagonist | ADORA2A | IC50 | 0.07545014 | uM | 1.3493 | −1.0713 | 99 | 98.542 |

Example 2

Pharmacokinetic data for compounds of formulae I, II, III, and IV.

Male CD-1 mice were given either bolus 1 mg/kg i.v. or 3 mg/kg p.o. of the indicated compounds and plasma or brain concentrations were measured.

Plasma concentrations following 1 mg/kg bolus i.v. administration of the compound of formula I.

| Experimental | Plasma concentration (ng/mL) | | | | |
|---|---|---|---|---|---|
| time (h) | 1 | 2 | 3 | Mean | SD |
| 0.0833 | 1080 | 981 | 908 | 990 | 86.3 |
| 0.25 | 587 | 540 | 837 | 655 | 160 |
| 0.5 | 516 | 527 | 489 | 511 | 19.6 |
| 1 | 377 | 417 | 318 | 371 | 49.8 |
| 2 | 278 | 264 | 280 | 274 | 8.72 |
| 4 | 150 | 212 | 253 | 205 | 51.9 |
| 6 | 106 | 202 | 161 | 156 | 48.2 |
| 8 | 122 | 153 | 141 | 139 | 15.6 |

Brain concentrations following 1 mg/kg bolus i.v. administration of the compound of formula I.

| Experimental | Brain concentration (ng/g) | | | | |
|---|---|---|---|---|---|
| time (h) | 1 | 2 | 3 | Mean | SD |
| 0.0833 | 818 | 851 | 682 | 784 | 89.6 |
| 0.25 | 373 | 426 | 665 | 488 | 156 |
| 0.5 | 377 | 282 | 381 | 347 | 56.0 |
| 1 | 269 | 318 | 175 | 254 | 72.7 |
| 2 | 159 | 195 | 185 | 180 | 18.6 |
| 4 | 120 | 158 | 198 | 159 | 39.0 |
| 6 | 91.2 | 138 | 122 | 117 | 23.8 |
| 8 | 110 | 118 | 114 | 114 | 4.00 |

Brain/plasma concentration ratios following 1 mg/kg bolus i.v. administration of 1a.

| Experimental | Brain/plasma concentration ratio | | | | |
|---|---|---|---|---|---|
| time (h) | 1 | 2 | 3 | Mean | SD |
| 0.0833 | 0.757 | 0.867 | 0.751 | 0.792 | 0.0654 |
| 0.25 | 0.635 | 0.789 | 0.795 | 0.740 | 0.0903 |
| 0.5 | 0.731 | 0.535 | 0.779 | 0.682 | 0.129 |
| 1 | 0.714 | 0.763 | 0.550 | 0.675 | 0.111 |
| 2 | 0.572 | 0.739 | 0.661 | 0.657 | 0.0834 |
| 4 | 0.800 | 0.745 | 0.783 | 0.776 | 0.0280 |

-continued

| Experimental | Brain/plasma concentration ratio | | | | |
|---|---|---|---|---|---|
| time (h) | 1 | 2 | 3 | Mean | SD |
| 6 | 0.860 | 0.683 | 0.758 | 0.767 | 0.0890 |
| 8 | 0.902 | 0.771 | 0.809 | 0.827 | 0.0672 |

FIG. 7 is a graph showing plasma and brain concentrations of the compound of Formula I over time.

Plasma concentrations following 3 mg/kg p.o. administration of the compound of formula I.

| Experimental | Plasma concentration (ng/mL) | | | | |
|---|---|---|---|---|---|
| time (h) | 1 | 2 | 3 | Mean | SD |
| 0.25 | 58.6 | 64.6 | 26.9 | 50.0 | 20.3 |
| 0.5 | 99.3 | 83.0 | 110 | 97.4 | 13.6 |
| 1 | 98.0 | 170 | 170 | 146 | 41.6 |
| 2 | 252 | 381 | 323 | 319 | 64.6 |
| 4 | 439 | 462 | 371 | 424 | 47.3 |
| 6 | 336 | 174 | 269 | 260 | 81.4 |
| 8 | 312 | 263 | 424 | 333 | 82.5 |
| 24 | 41.6 | 53.5 | 44.0 | 46.4 | 6.29 |

FIG. 8 is a graph showing the plasma concentrations over time after administration of 1 mg/kg i.v. or 3 mg/kg p.o of the compound of Formula I.

Summary of Plasma PK Parameters for the Compound of Formula I.

| | Estimate | |
|---|---|---|
| Parameter | i.v. | p.o. |
| $C_0$ (ng/mL) | 1217 | n/a[a] |
| $t_{max}$ (h) | 0.0833 | 4.00 |
| $C_{max}$ (ng/mL) | 990 | 424 |
| Apparent $t_{1/2}$ (h) | 6.00 | 6.52 |
| $AUC_{0\text{-}tlast}$ (h * ng/mL) | 2040 | 4651 |
| $AUC_{0\text{-}inf}$ (h * ng/mL) | 3244[b] | 5088 |
| CL (mL/h/kg) | 308[b] | n/a |
| $MRT_{0\text{-}inf}$ (h) | 8.02[b] | 11.1 |
| Vss (mL/kg) | 2472[b] | n/a |
| F (%) | 100 | 76.0[b] |

[a]n/a denotes not applicable; and
[b]As % AUC extrapolated from tlast to infinity is >20%, values are not considered accurate.

Summary of Brain PK Parameters for the Compound of Formula I.

| Parameter | Estimate |
|---|---|
| $t_{max}$ (h) | 0.0833 |
| $C_{max}$ (ng/g) | 784 |
| Apparent $t_{1/2}$ (h) | 8.27 |
| $AUC_{0-tlast}$ (h * ng/g) | 1,447 |
| $AUC_{0-inf}$ (h * ng/g) | 2807[a] |
| $MRT_{0-inf}$ (h) | 11.2[a] |
| Brain/plasma $AUC_{0-tlast}$ ratio | 0.710 |

[a]As % AUC extrapolated from tlast to infinity is >20%, values are not considered accurate.

For compound of formula I, the measured dosing solution concentration was 0.203 mg/mL and 0.296 for i.v. and p.o. formulations, respectively.

Where:

$C_0$ concentration extrapolated to time zero following an i.v. dose $t_{max}$ time at which maximum concentration is observed $C_{max}$ maximum observed concentration Apparent $t_{1/2}$ apparent terminal half-life $AUC_{0-tlast}$ area under the concentration vs time curve from time 0 to the time of the last measurable concentration $AUC_{0-inf}$ area under the concentration vs time curve from time 0 to infinity CL systemic clearance $MRT_{0-inf}$ mean residence time from time zero to infinity $V_{ss}$ steady-state volume of distribution F oral bioavailability=$(Dose^{iv}*AUC^{po})/(Dose^{po}*AUC^{iv})*100$ Plasma Concentrations Following 1 mg/kg Bolus i.v. Administration of the Compound of Formula II.

| Experimental | Plasma concentration (ng/mL) | | | | |
|---|---|---|---|---|---|
| time (h) | 1 | 2 | 3 | Mean | SD |
| 0.0833 | 599 | 667 | 587 | 618 | 43.1 |
| 0.25 | 583 | 713 | 729 | 675 | 80.1 |
| 0.5 | 494 | 404 | 315 | 404 | 89.5 |
| 1 | 244 | 356 | 344 | 315 | 61.5 |
| 2 | 214 | 172 | 275 | 220 | 51.8 |
| 4 | 150 | 142 | 143 | 145 | 4.36 |
| 6 | 35.9 | 39.4 | 57.0 | 44.1 | 11.3 |
| 8 | 32.2 | 38.3 | 39.0 | 36.5 | 3.74 |

Brain Concentrations Following 1 mg/kg Bolus i.v. Administration of the Compound of Formula II.

| Experimental | Brain concentration (ng/g) | | | | |
|---|---|---|---|---|---|
| time (h) | 1 | 2 | 3 | Mean | SD |
| 0.0833 | 428 | 550 | 442 | 473 | 66.8 |
| 0.25 | 314 | 385 | 235 | 311 | 75.0 |
| 0.5 | 293 | 188 | 162 | 214 | 69.4 |
| 1 | 208 | 143 | 187 | 179 | 33.2 |
| 2 | 120 | 92.9 | 146 | 120 | 26.6 |
| 4 | 119 | 101 | 106 | 109 | 9.29 |
| 6 | 39.7 | 41.9 | 52.5 | 44.7 | 6.84 |
| 8 | 43.7 | 38.7 | 47.8 | 43.4 | 4.56 |

Brain/Plasma Concentration Ratios Following 1 mg/kg Bolus i.v. Administration of the Compound of Formula II.

| Experimental | Brain/plasma concentration ratio | | | | |
|---|---|---|---|---|---|
| time (h) | 1 | 2 | 3 | Mean | SD |
| 0.0833 | 0.715 | 0.825 | 0.753 | 0.764 | 0.0559 |
| 0.25 | 0.539 | 0.540 | 0.322 | 0.467 | 0.125 |
| 0.5 | 0.593 | 0.465 | 0.514 | 0.524 | 0.0645 |
| 1 | 0.852 | 0.402 | 0.544 | 0.599 | 0.230 |
| 2 | 0.561 | 0.540 | 0.531 | 0.544 | 0.0153 |
| 4 | 0.793 | 0.711 | 0.741 | 0.749 | 0.0415 |
| 6 | 1.11 | 1.06 | 0.921 | 1.03 | 0.0968 |
| 8 | 1.36 | 1.01 | 1.23 | 1.20 | 0.175 |

FIG. 9 is a graph showing plasma and brain concentrations of the compound of Formula II over time.

Plasma Concentrations Following 3 mg/kg p.o. Administration of the Compound of Formula II.

| Experimental | Plasma concentration (ng/mL) | | | | |
|---|---|---|---|---|---|
| time (h) | 1 | 2 | 3 | Mean | SD |
| 0.25 | 116 | 136 | 106 | 119 | 15.3 |
| 0.5 | 225 | 156 | 82.8 | 155 | 71.1 |
| 1 | 264 | 320 | 421 | 335 | 79.6 |
| 2 | 288 | 292 | 247 | 276 | 24.9 |
| 4 | 363 | 469 | 289 | 374 | 90.5 |
| 6 | 181 | 185 | 178 | 181 | 3.51 |
| 8 | 118 | 138 | 97.7 | 118 | 20.2 |
| 24 | 2.83 | 2.92 | 1.78 | 2.51 | 0.634 |

FIG. 10 is a graph showing the plasma concentrations over time after administration of 1 mg/kg i.v. or 3 mg/kg p.o of the compound of Formula II.

Summary of Plasma PK Parameters for the Compound of Formula II.

| | Estimate | |
|---|---|---|
| Parameter | i.v. | p.o. |
| $C_0$ (ng/mL) | nc[a] | n/a[b] |
| $t_{max}$ (h) | 0.250 | 4.00 |
| $C_{max}$ (ng/mL) | 675 | 374 |
| Apparent $t_{1/2}$ (h) | 2.11 | 2.90 |
| $AUC_{0-tlast}$ (h*ng/ml) | 1344 | 2432 |
| $AUC_{0-inf}$ (h*ng/mL) | 1455 | 2443 |
| CL(mL/h/kg) | 687 | n/a |
| $MRT_{0-inf}$ (h) | 2.92 | 5.41 |
| Vss (mL/kg) | 2004 | n/a |
| F (%) | 100 | 56.0 |

[a]nc denotes not calculable as tmax was > the first time-point (0.0833 h), possibly due to TA precipitation following dosing; and
[b]n/a denotes not applicable.

Summary of Brain PK Parameters for the Compound of Formula II.

| Parameter | Estimate |
|---|---|
| $t_{max}$ (h) | 0.0833 |
| $C_{max}$ (ng/mL) | 473 |
| Apparent $t_{1/2}$ (h) | 3.52 |
| $AUC_{0-tlast}$ (h*ng/g) | 856 |
| $AUC_{0-inf}$ (h*ng/g) | 1076 |
| $MRT_{0-inf}$ (h) | 4.84 |
| Brain/plasma $AUC_{0-inf}$ ratio | 0.739 |

For compound of formula II, the measured dosing solution concentration was 0.193 mg/mL and 0.299 for i.v. and p.o. formulations, respectively.

Plasma Concentrations Following 1 mg/kg Bolus i.v. Administration of Formula III (SD-007).

| Experimental | Plasma concentration (ng/mL) | | | | |
|---|---|---|---|---|---|
| time (h) | 1 | 2 | 3 | Mean | SD |
| 0.0833 | 290 | 319 | 338 | 316 | 24.2 |
| 0.25 | 353 | 332 | 396 | 360 | 32.6 |
| 0.5 | 322 | 462 | 271 | 352 | 98.9 |
| 1 | 247 | 301 | 279 | 276 | 27.2 |
| 2 | 153 | 212 | 204 | 190 | 32.0 |
| 4 | 149 | 145 | 176 | 157 | 16.9 |
| 6 | 86.4 | 90.2 | 79.1 | 85.2 | 5.64 |
| 8 | 64.2 | 57.8 | 57.0 | 59.7 | 3.95 |

Brain Concentrations Following 1 mg/kg Bolus i.v. Administration of the Compound of Formula III.

| Experimental | Brain concentration (ng/g) | | | | |
|---|---|---|---|---|---|
| time (h) | 1 | 2 | 3 | Mean | SD |
| 0.0833 | 490 | 383 | 368 | 414 | 66.5 |
| 0.25 | 379 | 454 | 394 | 409 | 39.7 |
| 0.5 | 379 | 457 | 304 | 380 | 76.5 |
| 1 | 262 | 348 | 354 | 321 | 51.5 |
| 2 | 212 | 239 | 224 | 225 | 13.5 |
| 4 | 96.9 | 165 | 113 | 125 | 35.6 |
| 6 | 90.1 | 94.1 | 81.5 | 88.6 | 6.44 |
| 8 | 45.5 | 63.9 | 38.8 | 49.4 | 13.0 |

Brain/Plasma Concentration Ratios Following 1 mg/kg Bolus i.v. Administration of the Compound of Formula III.

| Experimental | Brain/plasma concentration ratio | | | | |
|---|---|---|---|---|---|
| time (h) | 1 | 2 | 3 | Mean | SD |
| 0.0833 | 1.69 | 1.20 | 1.09 | 1.33 | 0.320 |
| 0.25 | 1.07 | 1.37 | 0.995 | 1.15 | 0.196 |
| 0.5 | 1.18 | 0.989 | 1.12 | 1.10 | 0.0965 |
| 1 | 1.06 | 1.16 | 1.27 | 1.16 | 0.104 |
| 2 | 1.39 | 1.13 | 1.10 | 1.20 | 0.158 |
| 4 | 0.650 | 1.14 | 0.642 | 0.810 | 0.284 |
| 6 | 1.04 | 1.04 | 1.03 | 1.04 | 0.00733 |
| 8 | 0.709 | 1.11 | 0.681 | 0.832 | 0.238 |

FIG. 11 is a graph showing plasma and brain concentrations of the compound of Formula III over time.

Plasma Concentrations Following 3 mg/kg p.o. Administration of the Compound of Formula III.

| Experimental | Plasma concentration (ng/mL) | | | | |
|---|---|---|---|---|---|
| time (h) | 1 | 2 | 3 | Mean | SD |
| 0.25 | 29.0 | 29.6 | 46.0 | 34.9 | 9.65 |
| 0.5 | 78.1 | 65.1 | 41.6 | 61.6 | 18.5 |
| 1 | 152 | 132 | 89.1 | 124 | 32.1 |
| 2 | 83.2 | 76.1 | 99.2 | 86.2 | 11.8 |
| 4 | 102 | 121 | 92.2 | 105 | 14.6 |
| 6 | 55.9 | 63.7 | 79.0 | 66.2 | 11.8 |
| 8 | 54.4 | 32.1 | 91.6 | 59.4 | 30.1 |
| 24 | 5.19 | 6.58 | 1.24 | 4.34 | 2.77 |

FIG. 12 is a graph showing the plasma concentrations over time after administration of 1 mg/kg i.v. or 3 mg/kg p.o of the compound of Formula III.

Summary of Plasma PK Parameters for the Compound of Formula III.

| | Estimate | |
|---|---|---|
| Parameter | i.v. | p.o. |
| $C_0$ (ng/mL) | nc[a] | n/a[b] |
| $t_{max}$ (h) | 0.250 | 1.00 |
| $C_{max}$ (ng/mL) | 360 | 124 |
| Apparent $t_{1/2}$ (h) | 3.39 | 4.44 |
| $AUC_{0\text{-}tlast}$ (h*ng/ml) | 1282 | 988 |
| $AUC_{0\text{-}inf}$ (h*ng/mL) | 1575 | 1016 |
| CL(mL/h/kg) | 635 | n/a |
| $MRT_{0\text{-}inf}$ (h) | 4.73 | 7.55 |
| Vss (mL/kg) | 3000 | n/a |
| F (%) | 100 | 21.5 |

Summary of Brain PK Parameters for the Compound of Formula III.

| Parameter | Estimate |
|---|---|
| $t_{max}$ (h) | 0.0833 |
| $C_{max}$ (ng/mL) | 414 |
| Apparent $t_{1/2}$ (h) | 2.83 |
| $AUC_{0\text{-}tlast}$ (h*ng/g) | 1315 |
| $AUC_{0\text{-}inf}$ (h*ng/g) | 1517 |
| $MRT_{0\text{-}inf}$ (h) | 3.94 |
| Brain/plasma $AUC_{0\text{-}inf}$ ratio | 0.963 |

For compound of formula III, the measured dosing solution concentration was 0.196 mg/mL and 0.282 for i.v. and p.o. formulations, respectively.

Plasma Concentrations Following 1 mg/kg Bolus i.v. Administration of Istradefylline.

| Experimental | Plasma concentration (ng/mL) | | | | |
|---|---|---|---|---|---|
| time (h) | 1 | 2 | 3 | Mean | SD |
| 0.0833 | 751 | 612 | 648 | 670 | 72.1 |
| 0.25 | 647 | 872 | 716 | 745 | 115 |
| 0.5 | 596 | 441 | 774 | 604 | 167 |
| 1 | 421 | 452 | 361 | 411 | 46.3 |
| 2 | 241 | 294 | 242 | 259 | 30.3 |
| 4 | 123 | 69.7 | 77.1 | 89.9 | 28.9 |
| 6 | 66.6 | 35.2 | 37.9 | 46.6 | 17.4 |
| 8 | 12.1 | 11.1 | 8.65 | 10.6 | 1.78 |

Brain Concentrations Following 1 mg/kg Bolus i.v. Administration of Istradefylline.

| Experimental | Brain concentration (ng/g) | | | | |
|---|---|---|---|---|---|
| time (h) | 1 | 2 | 3 | Mean | SD |
| 0.0833 | 545 | 423 | 691 | 553 | 134 |
| 0.25 | 272 | 474 | 418 | 388 | 104 |
| 0.5 | 372 | 230 | 235 | 279 | 80.6 |
| 1 | 225 | 209 | 237 | 224 | 14.0 |
| 2 | 171 | 180 | 156 | 169 | 12.1 |

-continued

| Experimental | Brain concentration (ng/g) | | | | |
|---|---|---|---|---|---|
| time (h) | 1 | 2 | 3 | Mean | SD |
| 4 | 107 | 76.8 | 79.5 | 87.8 | 16.7 |
| 6 | 39.8 | 50.1 | 32.6 | 40.8 | 8.80 |
| 8 | 33.4 | 22.2 | 17.1 | 24.2 | 8.34 |

Brain/Plasma Concentration Ratios Following 1 mg/kg Bolus i.v. Administration of Istradefylline.

| Experimental | Brain/plasma concentration ratio | | | | |
|---|---|---|---|---|---|
| time (h) | 1 | 2 | 3 | Mean | SD |
| 0.0833 | 0.726 | 0.691 | 1.07 | 0.828 | 0.207 |
| 0.25 | 0.420 | 0.544 | 0.584 | 0.516 | 0.0851 |
| 0.5 | 0.624 | 0.522 | 0.304 | 0.483 | 0.164 |
| 1 | 0.534 | 0.462 | 0.657 | 0.551 | 0.0981 |
| 2 | 0.710 | 0.612 | 0.645 | 0.655 | 0.0495 |
| 4 | 0.870 | 1.10 | 1.03 | 1.00 | 0.119 |
| 6 | 0.598 | 1.42 | 0.860 | 0.960 | 0.422 |
| 8 | 2.76 | 2.00 | 1.98 | 2.25 | 0.446 |

FIG. 13 is a graph showing plasma and brain concentrations of the compound of Formula IV over time.

Plasma Concentrations Following 3 mg/kg p.o. Administration of Istradefylline.

| Experimental | Plasma concentration (ng/mL) | | | | |
|---|---|---|---|---|---|
| time (h) | 1 | 2 | 3 | Mean | SD |
| 0.25 | 34.8 | 55.4 | 38.5 | 42.9 | 11.0 |
| 0.5 | 61.8 | 87.1 | 111 | 86.6 | 24.6 |
| 1 | 241 | 225 | 285 | 250 | 31.1 |
| 2 | 209.0 | 108 | 321 | 213 | 107 |
| 4 | 192 | 291 | 249 | 244 | 49.7 |
| 6 | 201 | 139 | 68.6 | 136 | 66.2 |
| 8 | 15.7 | 8.97 | 22.4 | 15.7 | 6.72 |
| 24 | *0.255* | BLQ | *0.249* | 0.252 | n/a |

Values in italics are below the lower level of quantitation (BLQ, 0.5 ng/mL) but were included in calculations; BLQ denotes below the lower level of quantitation (0.5 ng/mL); and n/a denotes not applicable.

FIG. 14 is a graph showing the plasma concentrations over time after administration of 1 mg/kg i.v. or 3 mg/kg p.o of the compound of Formula IV, Istradefyline.

Summary of Plasma PK Parameters for Istradefylline.

| Parameter | Estimate | |
|---|---|---|
| | i.v. | p.o. |
| $C_0$ (ng/mL) | nc[a] | n/a[b] |
| $t_{max}$ (h) | 0.250 | 1.00 |
| $C_{max}$ (ng/mL) | 745 | 250 |
| Apparent $t_{1/2}$ (h) | 1.35 | 2.20 |
| $AUC_{0\text{-}tlast}$ (h*ng/ml) | 1422 | 1335 |
| $AUC_{0\text{-}inf}$ (h*ng/mL) | 1442 | 1335 |
| CL(mL/h/kg) | 693 | n/a |
| $MRT_{0\text{-}inf}$(h) | 1.96 | 3.82 |
| Vss (mL/kg) | 1362 | n/a |
| F (%) | 100 | 30.9 |

Summary of Brain PK Parameters for Istradefylline.

| Parameter | Estimate |
|---|---|
| $t_{max}$ (h) | 0.0833 |
| $C_{max}$ (ng/mL) | 553 |
| Apparent $t_{1/2}$ (h) | 2.10 |
| $AUC_{0\text{-}tlast}$ (h*ng/g) | 938 |
| $AUC_{0\text{-}inf}$ (h*ng/g) | 1011 |
| $MRT_{0\text{-}inf}$ (h) | 2.96 |
| Brain/plasma $AUC_{0\text{-}inf}$ ratio | 0.701 |

[a]nc denotes not calculable as tmax was > the first time-point (0.0833 h), possibly due to TA precipitation following dosing; and
[b]n/a denotes not applicable.

For compound of formula IV, the measured dosing solution concentration was 0.221 mg/mL and 0.325 for i.v. and p.o. formulations, respectively.

Example 3

Figure 16:
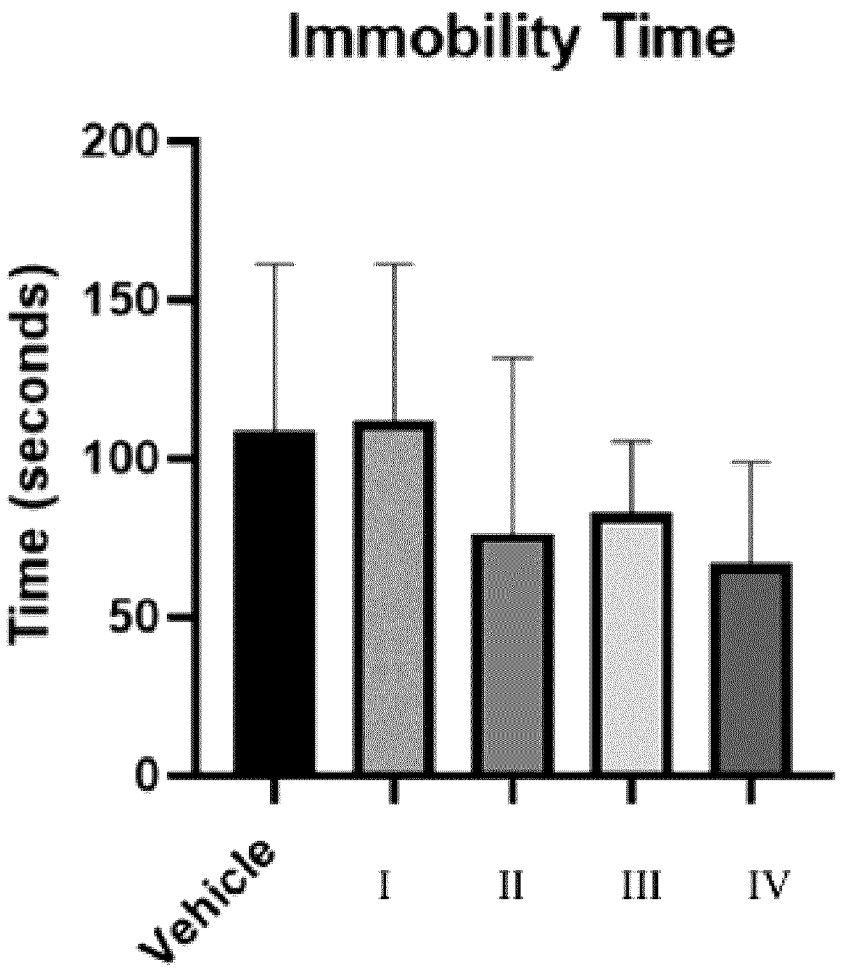
FIG. 16 is a graph comparing the immobility time for various compounds.

The compounds of formulae I, II, III, and IV were tested in a study of depression using mice and the forced swim test. The results are shown in FIGS. 15 and 16.

The forced swim test, also known as the behavioral despair test, is used to test for depression-like behavior. The test includes placing a rat or mouse inside a cylinder filled with water. 'Floating behavior' (where the animal remains almost immobile and with its head above water) is used as a parameter to analyze 'hopelessness' and thus depression-like behavior. Rodents given antidepressants swim longer than controls. Immobility time is decreased by various antidepressants.

40 male CD-1 mice (N=8 mice per group) were treated orally with either vehicle (0.3% Tween 80) or test article (1 mg/kg) of formula I (target 1a), II (target 1b), III (SD-007) or IV (Istradefylline, KW-6002) one hour prior to testing. At t=0, mice were placed in a glass cylinder filled with water. After a period of vigorous activity, the mouse would adopt a characteristic immobile posture which is readily scored. Over a 6-minute test session, the latency to first immobility is recorded (in seconds). The duration of immobility (in seconds) during the last 4 minutes of the test is also measured.

Formula II statistically significantly delayed the time to immobility (One-way ANOVA with Dunnett's multiple comparisons test). A similar effect of Formula II and IV was seen in the immobility time (2-6 minutes). Thus efficacy of these compounds in reducing depression-like behavior was demonstrated.

The embodiments of the present disclosure described above are intended to be examples only. The present disclosure may be embodied in other specific forms. Alterations, modifications and variations to the disclosure may be made without departing from the intended scope of the present disclosure. While the system, devices and processes disclosed and shown herein may comprise a specific number of elements/components, the systems, devices and assemblies could be modified to include addition or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

The invention claimed is:

1. A compound of formula (II)

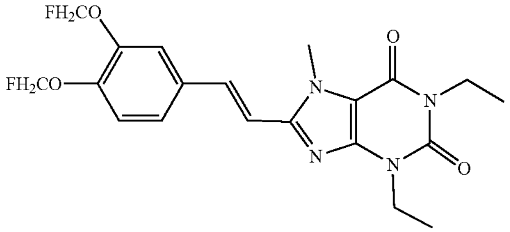

or a pharmaceutically acceptable salt thereof.

2. A method for treating depression, the method comprising administration of the compound of claim 1.

3. A method for treating a subject having one or more of depression, anxiety, and Parkinsons, the method comprising administration of an effective amount of the compound of claim 1.

4. The method of claim 2, wherein the administration is oral.

5. The method of claim 2, wherein the administration is injection.

6. The method of claim 3, wherein the administration is oral.

7. The method of claim 3, wherein the administration is injection.

8. A composition comprising the compound of claim 1, with a pharmaceutically acceptable excipient.

9. A pharmaceutical composition for treating depression, the composition comprising the compound of claim 1.

10. A pharmaceutical composition for treating depression, anxiety, or Parkinsons, the composition comprising the compound of claim 1 and a pharmaceutically acceptable excipient.

11. A pharmaceutical composition comprising the compound of claim 1 and a pharmaceutically acceptable excipient.

* * * * *